United States Patent
Park et al.

(10) Patent No.: US 11,117,931 B2
(45) Date of Patent: Sep. 14, 2021

(54) ANTIMICROBIAL PEPTIDE DERIVED FROM HP1404 PEPTIDE AND USES THEREOF

(71) Applicant: INDUSTRY-ACADEMIC COOPERATION FOUNDATION, CHOSUN UNIVERSITY, Gwangju (KR)

(72) Inventors: Yoonkyung Park, Jeollanam-do (KR); Min-Kyung Kim, Jeollanam-do (KR)

(73) Assignee: INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 0 days.

(21) Appl. No.: 16/648,060

(22) PCT Filed: Sep. 21, 2018

(86) PCT No.: PCT/KR2018/011241
§ 371 (c)(1),
(2) Date: Mar. 17, 2020

(87) PCT Pub. No.: WO2019/059709
PCT Pub. Date: Mar. 28, 2019

(65) Prior Publication Data
US 2020/0216497 A1    Jul. 9, 2020

(30) Foreign Application Priority Data
Sep. 22, 2017  (KR) .................... 10-2017-0122504

(51) Int. Cl.
| | |
|---|---|
| *A61K 38/10* | (2006.01) |
| *A61K 31/00* | (2006.01) |
| *A61K 31/43* | (2006.01) |
| *A61K 38/00* | (2006.01) |
| *A61K 45/06* | (2006.01) |
| *A61K 8/64* | (2006.01) |
| *A61P 31/04* | (2006.01) |
| *C07K 7/08* | (2006.01) |
| *A23K 20/147* | (2016.01) |
| *A01N 37/46* | (2006.01) |

(52) U.S. Cl.
CPC ................ *C07K 7/08* (2013.01); *A01N 37/46* (2013.01); *A23K 20/147* (2016.05); *A61K 8/64* (2013.01); *A61P 31/04* (2018.01); *A61K 38/00* (2013.01); *A61K 45/06* (2013.01)

(58) Field of Classification Search
CPC .... A61K 2300/00; A61K 38/10; A61K 31/00; A61K 31/165; A61K 31/43; A61K 31/7048; A61K 38/00; A61K 45/06; A61K 8/64; A61P 31/04; A61Q 17/005; C07K 7/08
USPC .... 514/1.1, 2.4, 2.6, 2.7, 2.8, 21.5; 530/327, 530/300
See application file for complete search history.

(56) References Cited

U.S. PATENT DOCUMENTS 5,294,605 A * 3/1994 Houghten ............... C07K 14/46
                                              514/19.3
7,550,430 B2 * 6/2009 Keeler .......................... 514/1.1

FOREIGN PATENT DOCUMENTS

| KR | 10-0308861 B1 | 12/2001 |
| KR | 10-2010-0054361 A | 5/2010 |
| KR | 10-2012-0051862 A | 5/2012 |
| KR | 10-2013-0081989 A | 7/2013 |

OTHER PUBLICATIONS

International Search Report for PCT/KR2018/011241 dated Apr. 22, 2019.
Li, Z. et al., "K1K8: an Hp1404-derived antibacterial peptide", Appl Microbiol Biotechnol., vol. 100, No. 11, p. 5069-5077, 2016.
Thomas E. Creighton, "Proteins; structures and molecular principles.", W. H. Freeman and Company New York, p. 286-295, 1983.
Merrifield, RB., "Solid Phase Peptide Synthesis I. The Synthesis of a Tetrapeptide", J. Am. Chem. Soc., 85: p. 2149-2154, 1963.

* cited by examiner

*Primary Examiner* — Julie Ha
(74) *Attorney, Agent, or Firm* — The PL Law Group, PLLC

(57) ABSTRACT

An antimicrobial peptide has the amino acid sequence of SEQ ID NO: 1, except that i) the 1st and the 14th amino acids are deleted, ii) the 4th and the 8th amino acids are substituted with lysine (K), iii) the 7th amino acid is substituted with leucine (L), iv) the 9th amino acid is optionally substituted with lysine (K), and v) the 12th amino acid is optionally substituted with lysine (K). A method for antimicrobial treatment in a subject including administering a pharmaceutically effective amount of the antimicrobial peptide to a subject.

20 Claims, 8 Drawing Sheets
Specification includes a Sequence Listing.

ANTIMICROBIAL PEPTIDE DERIVED FROM HP1404 PEPTIDE AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/011241 filed on Sep. 21, 2018, which claims priority to the benefit of Korean Patent Application No. 10-2017-0122504 filed in the Korean Intellectual Property Office on Sep. 22, 2017, the entire contents of which are incorporated herein by reference.

TECHNICAL FIELD

The present invention relates to a novel antimicrobial peptide derived from Hp1404 peptide and uses thereof.

BACKGROUND ART

Bacterial infection is one of the most common and deadly causes of a human disease. Unfortunately, due to abuse of antibiotics, bacterial resistance to antibiotics has been yielded. The rate of exhibiting resistance to antibiotics by bacteria is indeed much faster than the rate of developing new homologues of the antibiotics. For example, various bacterial species like *Enterococcus faecalis*, *Mycobacterium tuberculosis*, and *Pseudomonas aeruginosa*, which may pose a threat to human life, have developed resistance to all antibiotics that are known until now.

Antibiotic tolerance is a phenomenon that is distinguished from the resistance to antibiotics, and after being found first in *Pneumococcus* sp. in 1970s, it provides an important clue for studying the working mechanism of penicillin. Bacterial species exhibiting the tolerance show growth stall in the presence of antibiotics at common concentration, but without any death. The tolerance is caused due to a lack of the activity of an autolytic bacterial enzyme like autolysin as the antibiotics inhibit an enzyme for synthesizing cell wall, and this leads to the results that, as an endogenous hydrolytic enzyme is activated by penicillin, bacterial cell death is caused, and the bacteria also suppress the enzyme activity to survive even under a treatment with antibiotics.

Having bacterial tolerance to various antibiotics is clinically very important, because, once it becomes impossible to eradicate bacteria with tolerance, usefulness of a clinical treatment with antibiotics for infection is impaired. Furthermore, having tolerance is believed to a prerequisite requirement for developing resistance to antibiotics, and that is because there are bacterial strains which manage to survive even after a treatment with antibiotics. By acquiring new genetic elements to exhibit resistance to antibiotics, those bacterial strains keep growing even in the presence of the antibiotics. Since all bacteria exhibiting resistance are indeed known to have tolerance too, it is necessary to develop novel antibiotics which can be used for eradicating those bacteria having resistance to antibiotics.

In terms of working mechanism, the tolerance to antibiotics broadly consists of two pathways. The first pathway is phenotypic tolerance which occurs during every bacteria growth with decreasing rate, and the second pathway is genetic tolerance caused by mutation which occurs in specific types of bacteria. In all of those cases, the basic phenomenon is an occurrence of down regulation of autolysin activity. This down regulation is transient in case of phenotypic tolerance against external stimulation, while it is permanent in case of genetic tolerance in which there is an occurrence of a mutation for causing a change in pathway for regulating cell lysis. The simplest genetic tolerance is based on a defect in autolysin enzyme, and due to various kinds of reasons which have not been clarified, a bacterial strain having the tolerance as caused by a defect in autolysin has not been clinically found yet, and clinical tolerance is rather achieved via regulation of the activity of autolysin.

As discussed in the above, in order to deal with bacteria which exhibit resistance to antibiotics, development of new antibiotics is required, and also development of new antibiotics which work independently of the activity of autolysin is required.

Meanwhile, by synthesizing peptides or small organic molecules, bacteria may kill neighboring bacteria, and, in terms of the structure, those bacteriocins are categorized into three classes. First class is lantibiotics, second class is nonlantibiotics, and third class is those secreted by signal peptides. Animals including insects also produce peptide antibiotics that are naturally produced, and those antibiotics are categorized into three groups based on their structure. First group is cysteine-rich 3-sheet peptides, second group is α-helical amphipathic molecules, and third group is proline-rich peptides. Those antibiotic peptides are known to play an important role in host defense and innate immune system. Those antibiotic peptides have various structures depending on their amino acid sequence, and among those structures, Hp1404 as an antimicrobial peptide found in a scorpion forms an amphipathic α-helical structure.

Meanwhile, in Korean Patent Registration No. 1006321, "Antimicrobial peptide having antibiotic activity extracted from venom of *Orancistrocerus drewseni saussure* and gene encoding the same" is disclosed, and, in Korean Patent Registration No. 1440112, "Use of antibiotic coprisin peptide isolated from *Copris tripartitus* as antibacterial and antiinflammatory agent" is disclosed. However, the novel antimicrobial peptide derived from Hp1404 and uses thereof as described in the present invention have never been disclosed before.

SUMMARY

The present invention is devised under the circumstances described above. Specifically, to produce a novel synthetic peptide with enhanced antimicrobial activity from an antimicrobial peptide which has been previously reported, the inventors of the present invention synthesized 6 types of Hp1404 homologues (i.e., SEQ ID NO: 2 to SEQ ID NO: 7) by using the amphipathic Hp1404 antimicrobial peptide as a template, and found that, among the synthesized peptide homologues, Hp1404-T1c, Hp1404-T1d and Hp1404-T1e peptides (SEQ ID NO: 5 to SEQ ID NO: 7) have an excellent antimicrobial activity for Gram-positive bacteria, Gram-negative bacteria, and tolerant bacteria, and they exhibit low cytotoxicity for mouse erythrocytes and a human normal cell line (HaCaT). The present invention is completed accordingly.

In order to solve the problems described above, the present invention provides an antimicrobial peptide in which, in the amino acid sequence of SEQ ID NO: 1,
i) the $1^{st}$ and the $14^{th}$ amino acids are deleted,
ii) the $4^{th}$ and the $8^{th}$ amino acids are substituted with lysine (K),
iii) the $7^{th}$ amino acid is substituted with leucine (L),
iv) the $9^{th}$ amino acid is glycine (G) or substituted with lysine (K), and v) the 12$^{th}$ amino acid is serine (S) or substituted with lysine (K).

The present invention further provides antibiotics comprising the aforementioned antimicrobial peptide as an effective component.

The present invention further provides an antibiotic cosmetic composition comprising the aforementioned antimicrobial peptide as an effective component.

The present invention further provides an antibiotic food additive comprising the aforementioned antimicrobial peptide as an effective component.

The present invention further provides an antibiotic animal feed additive comprising the aforementioned antimicrobial peptide as an effective component.

The present invention further provides antibiotic biopesticides comprising the aforementioned antimicrobial peptide as an effective component.

The present invention further provides an antibiotic quasi-drug composition comprising the aforementioned antimicrobial peptide as an effective component.

The present invention still further provides a method for antimicrobial treatment in a subject including administering a pharmaceutically effective amount of the aforementioned antimicrobial peptide to a subject.

As the novel antimicrobial peptide (Hp1404-T1c, Hp1404-T1d and Hp1404-T1e) of the present invention has not only an excellent antimicrobial activity but also low cytotoxicity, it can be advantageously used as an effective component of anti-microbial antibiotics, cosmetic composition, food additive, animal feed additive, biopesticides, quasi-drug, and the like.

DETAILED DESCRIPTION

Figure 1:
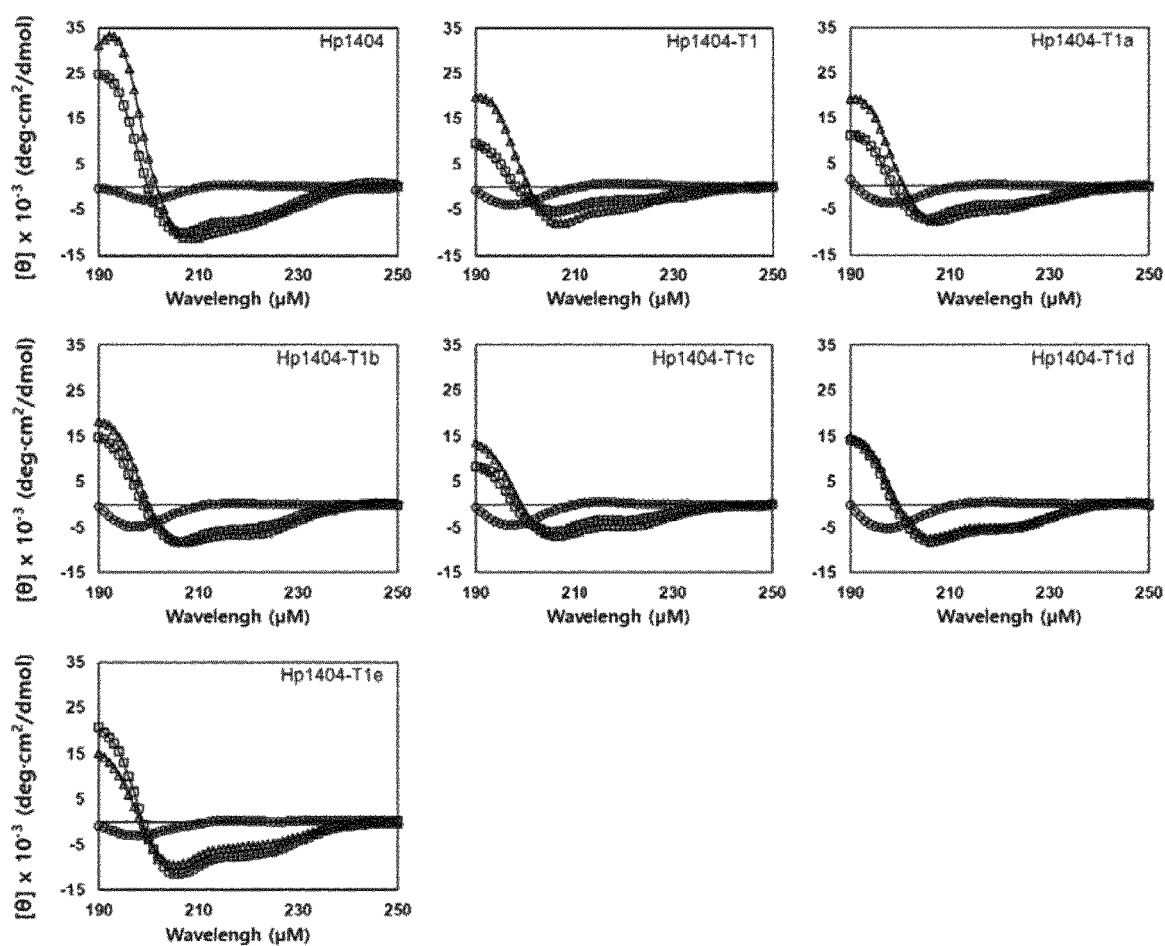
FIG. 1 shows the result of determining the forming of a secondary structure of antimicrobial peptide Hp1404 (control group) and antimicrobial peptide Hp1404-T1, Hp1404-T1a, Hp1404-T1b, Hp1404-T1c, Hp1404-T1d and Hp1404-T1e (test group), which are novel Hp1404 homologue peptides, in various solvents, in which ○ represents 10 mM sodium phosphate solution, □ represents 30 mM sodium dodecyl sulfate solution, and Δ represents 50% trifluoroethanol solution.

To achieve the purpose of the present invention, the present invention provides an antimicrobial peptide in which, in the amino acid sequence of SEQ ID NO: 1,
  i) the 1$^{st}$ and the 14$^{th}$ amino acids are deleted,
  ii) the 4$^{th}$ and the 8$^{th}$ amino acids are substituted with lysine (K),
  iii) the 7$^{th}$ amino acid is substituted with leucine (L),
  iv) the 9$^{th}$ amino acid is glycine (G) or substituted with lysine (K), and
  v) the 12$^{th}$ amino acid is serine (S) or substituted with lysine (K).

Hp1404 peptide as a mother peptide having the previously known amino acid sequence of SEQ ID NO: 1 is an antimicrobial peptide isolated from Asian forest scorpion (scorpion *Heterometrus petersii*), and it can be produced by a method for synthesizing peptide well known in the pertinent art. The production method is not particularly limited. As for the method for synthesis, synthesis is preferably carried out according to a method for chemical synthesis of a peptide that is commonly employed in the pertinent art (W. H. Freeman and Co., Proteins; structures and molecular principles, 1983). More preferably, synthesis is carried out by a solution phase peptide synthesis, a solid-phase peptide synthesis, a fragment condensation method, or F-moc or T-BOC chemical method. Most preferably, synthesis is carried out by a solution phase peptide synthesis, but it is not limited thereto.

The antimicrobial peptide of the present invention needs to satisfy the requirements i), ii), iii), iv) and v) described above. Specifically, in case of the requirement i), it is necessary that glycine (G) and phenylalanine (F), which are the 1$^{st}$ and the 14$^{th}$ amino acids of the mother peptide of SEQ ID NO: 1, respectively, are all deleted, and, in case of the requirement ii), it is necessary that glycine (G) and glutamic acid (E), which are the 4$^{th}$ and the 8$^{th}$ amino acids of the mother peptide of SEQ ID NO: 1, respectively, are substituted with lysine (K) as a basic amino acid having positive charge.

Next, in case of the requirement iii), tryptophan (W), which is the 7$^{th}$ amino acid of the mother peptide of SEQ ID NO: 1, is substituted with leucine (L), in which leucine is an amino acid having non-polar aliphatic R group.

Next, in case of the requirement (iv), glycine (G), which is the 9$^{th}$ amino acid of the mother peptide of SEQ ID NO: 1, remains unchanged, or is substituted with lysine (K) as a basic amino acid having positive charge.

Finally, in case of the requirement v), it is necessary that serine (S), which is the 12$^{th}$ amino acid of the mother peptide of SEQ ID NO: 1, remains unchanged, or is substituted with lysine (K) as a basic amino acid having positive charge.

As such, the case satisfying the requirements iv) and v) includes not only a case in which the 9$^{th}$ and 12$^{th}$ amino acids are glycine (G) and serine (S), respectively, but also a case in which the 9$^{th}$ and 12$^{th}$ amino acids are lysine (K) and serine (S), respectively, and a case in which both the $9^{th}$ and $12^{th}$ amino acids are lysine (K).

The antimicrobial peptide of the present invention preferably has the amino acid sequence of SEQ ID NO: 5 to SEQ ID NO: 7. Peptide having the amino acid sequence of SEQ ID NO: 5 is an antimicrobial peptide in which the $1^{st}$ and the $14^{th}$ amino acids are deleted from Hp1404 as a mother peptide, the $4^{th}$ and the $8^{th}$ amino acids are substituted with lysine (K), and the $7^{th}$ amino acid is substituted with leucine (L), and the peptide is named Hp1404-T1c. Peptide having the amino acid sequence of SEQ ID NO: 6 is an antimicrobial peptide in which the $1^{st}$ and the $14^{th}$ amino acids are deleted from Hp1404 as a mother peptide, the $4^{th}$, the $8^{th}$, and the $9^{th}$ amino acids are substituted with lysine (K), and the $7^{th}$ amino acid is substituted with leucine (L), and the peptide is named Hp1404-T1d. Peptide having the amino acid sequence of SEQ ID NO: 7 is an antimicrobial peptide in which the $1^{st}$ and the $14^{th}$ amino acids are deleted from Hp1404 as a mother peptide, the $4^{th}$, the $8^{th}$, the $9^{th}$, and the $12^{th}$ amino acids are substituted with lysine (K), and the $7^{th}$ amino acid is substituted with leucine (L), and the peptide is named Hp1404-T1e.

The antimicrobial peptide is most preferably a peptide consisting of any one amino acid sequence selected from the group consisting of the amino acid sequences of SEQ ID NO: 5 to SEQ ID NO: 7, but it is not limited thereto. According to utilization of increase/decrease of electric charge, the substitution can lower the cytotoxicity, and the substitution may be carried out to enhance or maintain the antimicrobial activity against Gram-negative bacteria and Gram-positive bacteria.

It is preferable that the antimicrobial peptide has an antimicrobial activity against Gram-negative bacteria, Gram-positive bacteria, or bacteria having tolerance to antibiotics, but it is not limited thereto.

Gram-negative bacteria are every Gram-negative bacteria that are known in the pertinent art including Gram-negative bacteria of *Pseudomonas* sp., *Escherichia* sp., *Salmonella* sp., *Leptospira* sp., and *Rickettsia* sp. Gram-negative bacteria are more preferably at least one selected from the group consisting of *Pseudomonas* sp and *Escherichia* sp. Gram-negative bacteria are most preferably *Pseudomonas aeruginosa*, but they are not limited thereto.

Gram-positive bacteria are every Gram-positive bacteria that are known in the pertinent art including Gram-positive bacteria of *Staphylococcus* sp., *Listeria* sp., *Corynebacterium* sp., *Lactobacillus* sp., and *Bacillus* sp. Gram-positive bacteria are more preferably Gram-positive bacteria of *Staphylococcus* sp. or *Listeria* sp. Gram-positive bacteria are most preferably *Staphylococcus aureus*, but they are not limited thereto.

The bacteria having tolerance to antibiotics are preferably at least one selected from the group consisting of *Pseudomonas aeruginosa, Escherichia coli*, and *Staphylococcus aureus* having tolerance to antibiotics, but they are not limited thereto.

Examples of the antibiotics include, although not limited thereto, aminoglycoside-based (aminoglycoside, gentamycin, neomycin, and the like), penicillin-based (ampicillin and the like), sulfonamide-based, beat-lactam based (beta-lactam, amoxicillin/clavulanic acid, and the like), chloramphenicol-based, erythromycin-based, florfenicol-based, fosfmycin-based, kanamycin-based, lincomycin-based, meticillin-based, quinolone-based, streptomycin-based, tetracycline-based, trimethoprim-based, and vancomycin-based antibiotics.

The antimicrobial peptide may exhibit low cytotoxicity for cells derived from mouse or human, but it is not limited thereto.

The present invention further provides antibiotics comprising the aforementioned antimicrobial peptide as an effective component. The antimicrobial peptide is preferably a peptide having any one amino acid sequence selected from the group consisting of the amino acid sequences of SEQ ID NO: 5 to SEQ ID NO: 7, and it is the same as described above.

Since Hp1404-T1c (SEQ ID NO: 5), Hp1404-T1d (SEQ ID NO: 6), and Hp1404-T1e peptides (SEQ ID NO: 7), which are an homologue antimicrobial peptide derived from Hp1404 antimicrobial peptide of the present invention, exhibit low cytotoxicity for cells derived from human while having a strong antimicrobial activity, the antimicrobial peptide of the present invention can be advantageously used as an effective component of antibacterial antibiotics.

For clinical administration, the peptide of the present invention can be administered parenterally, and it can be used in the form of a common pharmaceutical preparation. Parenteral administration may mean administration via a route other than oral administration like rectal, intravenous, intraperitoneal, intramuscular, intraarterial, transdermal, nasal, inhalational, intraocular, and subcutaneous administration. When the antimicrobial peptide of the present invention is used as a pharmaceutical, one or more effective components exhibiting the same or similar activity may be additionally included.

Namely, the antimicrobial peptide of the present invention can be indeed administered as various parenteral preparations, and, in case of having a preparation, production is made by using a diluent or a vehicle such as filler, bulking agent, binding agent, moisturizing agent, disintegrating agent, or surfactant that are commonly used for producing a preparation. In a preparation for parenteral administration, a sterilized aqueous solution, a non-soluble preparation, a suspension, an oil preparation, a freeze-dried preparation, and a suppository are included. As a water insoluble solvent or a suspending solvent, propylene glycol, polyethylene glycol, or vegetable oil such as olive oil, and injectable ester such as ethylolate can be used. As abase for a suppository, witepsol, macrogol, tween 61, cacao fat, laurin fat, glycerogelatin, or the like can be used.

Furthermore, the antimicrobial peptide of the present invention can be used after being admixed with various pharmaceutically acceptable carriers such as physiological saline or organic solvent. To enhance the stability or absorption property, carbohydrates such as glucose, sucrose, or dextran, anti-oxidants such as ascorbic acid or glutathione, chelating agents, low molecular weight proteins, or other stabilizers can be used as a pharmaceutical agent.

Effective dose of the antimicrobial peptide of the present invention is 0.1 to 2 mg/kg, and preferably 0.5 to 1 mg/kg. Administration can be made 1 to 3 times a day.

Total effective amount of the novel peptide of the present invention in the antibiotics of the present invention can be administered to a patient as a single dose in bolus form or infusion during a relatively short period of time, and it can be also administered according to a fractionated treatment protocol by which multiple dose is administered for a long period of time. With regard to the concentration described above, the effective dose is determined by considering not only the pharmaceutical administration route and number of treatment but also other various factors including age, health state, or the like of a patient. Thus, by considering them, a person having common knowledge in the pertinent art may determine suitable effective dose depending on specific use of the novel peptide of the present invention as antibiotics.

The present invention further provides an antibiotic cosmetic composition comprising the aforementioned antimicrobial peptide as an effective component.

The antimicrobial peptide is preferably a peptide having any one amino acid sequence selected from the group consisting of the amino acid sequences of SEQ ID NO: 5 to SEQ ID NO: 7, and it is the same as described above. This peptide exhibits low cytotoxicity for cells derived from human while showing a strong antimicrobial activity. As such, the antimicrobial peptide of the present invention can be advantageously used as an effective component of a cosmetic composition.

In the cosmetic composition of the present invention, components commonly used for a cosmetic composition are included in addition to the antimicrobial peptide, and examples thereof include a common auxiliary agent such as an anti-oxidant, a stabilizing agent, a solubilizing agent, vitamin, a pigment, or a fragrance, and a carrier.

In the cosmetic composition of the present invention, the peptide of the present invention may be added in an amount of 0.1 to 50% by weight, and preferably 1 to 10% by weight to the cosmetic composition.

The cosmetic composition of the present invention may be produced in any formulation that is produced commonly in the pertinent art. For example, it can be produced as a formulation such as a solution, a suspension, an emulsion, paste, gel, cream, lotion, powder, a soap, a surfactant-containing cleanser, oil, powder foundation, emulsion foundation, wax foundation, or spray, but it is not limited thereto. More specifically, it can be produced as a formulation such as softening cosmetic water (skin water), nutritive cosmetic water (milk lotion), nutritive cream, massage cream, essence, eye cream, cleansing cream, cleansing foam, cleansing water, pack, spray, or powder.

When the formulation of the present invention is paste, cream, or gel, animal oil, vegetable oil, wax, paraffin, starch, tragacanth, cellulose derivatives, polyethylene glycol, silicone, bentonite, silica, talc, or zinc oxide can be used as a carrier component.

When the formulation of the present invention is powder or spray, lactose, talc, silica, aluminum hydroxide, calcium silicate, or polyamide powder can be used as a carrier component. When the formulation is spray, in particular, a propellant such as chlorofluorohydrocarbon, propane/butane, or dimethyl ether may be additionally included.

When the formulation of the present invention is a solution or an emulsion, a solvent, a solubilizing agent, or an emulsifying agent is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

When the formulation of the present invention is a suspension, a liquid diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, or tragacanth can be used as a carrier component.

When the formulation of the present invention is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamine, vegetable oil, lanolin derivatives, or ethoxylated glycerol fatty acid ester can be used as a carrier component.

The present invention further provides an antibiotic food additive comprising the aforementioned antimicrobial peptide as an effective component.

The antimicrobial peptide is preferably a peptide having any one amino acid sequence selected from the group consisting of the amino acid sequences of SEQ ID NO: 5 to SEQ ID NO: 7, and it is the same as described above. This peptide exhibits low cytotoxicity for cells derived from human while showing a strong antimicrobial activity. As such, the antimicrobial peptide of the present invention can be advantageously used as an effective component of a food additive.

When the peptide of the present invention is used as a food additive, the peptide may be directly added or used with other food components, and it can be suitably used according to a general method. Blending amount of the effective component can be suitably determined depending on the purpose of use. In general, the peptide of the present invention is added in an amount of 15 parts by weight or less, and preferably 10 parts by weight or less relative to peptide raw materials. However, in case of application for a long period of time, the blending amount may be lower than the aforementioned range. As there is no problem in terms of the stability, the effective component may be used in an amount that is higher than the aforementioned range.

Type of the food is not particularly limited. Examples of the food to which the additive can be added include meat, sausage, bread, chocolate, candies, snacks, biscuits, pizza, ramen, other noodles, gums, dairy products including ice cream, various kinds of soup, beverage, tea, drink, alcohol beverage, and vitamin complex, and all foods in general sense are included therein.

The present invention further provides an antibiotic animal feed additive comprising the aforementioned antimicrobial peptide as an effective component.

The antimicrobial peptide is preferably a peptide having any one amino acid sequence selected from the group consisting of the amino acid sequences of SEQ ID NO: 5 to SEQ ID NO: 7, and it is the same as described above. This peptide exhibits low cytotoxicity for cells derived from human while showing a strong antimicrobial activity. As such, the antimicrobial peptide of the present invention can be advantageously used as an effective component of an animal feed additive.

The animal feed composition of the present invention has an effect of replacing existing antibiotics, inhibiting the growth of harmful pathogenic food bacteria to improve the health state of an animal, enhancing the body weight and meat quality of livestock, and enhancing the milk production amount and immunity of livestock. The animal feed composition of the present invention can be produced in the form of fermented animal feed, complete animal feed, pellets, silage, or the like.

The fermented animal feed can be produced by adding various microbes or enzymes other than the peptide of the present invention to ferment organic matters, and the complete animal feed can be produced by admixing the peptide of the present invention with various kinds of common animal feed. Animal feed in pellet form can be produced by applying heat and pressure to a complete feed in a pelletizing machine, and silage can be produced by fermenting forage with the microbes of the present invention. Fermented wet animal feed can be produced by, after collecting and transporting organic matters and admixing them with a vehicle at a certain ratio for moisture control and sterilization, fermenting organic matters like food waste at a temperature suitable for fermentation for 24 hours or longer to adjust moisture content to about 70%. Fermented dry animal feed can be produced according to adjustment of the moisture content to 30% to 40% or so by providing fermented wet animal feed additionally to a drying process.

The present invention further provides a preservative composition, antibiotic biopesticides, and an antibiotic quasi-drug composition comprising the aforementioned antimicrobial peptide as an effective component.

The antimicrobial peptide is preferably a peptide having any one amino acid sequence selected from the group consisting of the amino acid sequences of SEQ ID NO: 5 to SEQ ID NO: 7, and it is the same as described above. This peptide exhibits low cytotoxicity for cells derived from human while showing a strong antimicrobial activity. As such, the antimicrobial peptide of the present invention can be advantageously used as an effective component of antibiotic biopesticides, a preservative composition, or an antibiotic quasi-drug composition.

Examples of the preservative composition include a cosmetics preservative and a pharmaceutical preservative. The preservative agent for food, cosmetics preservative, and pharmaceutical preservative are an additive which is used to prevent deterioration, degradation, discoloration, and chemical change of those products, and examples thereof include a sterilizer and an anti-oxidant. Also included are functional antibiotics having an activity of inhibiting growth or sterilizing degrading bacteria in food product and pharmaceutical product according to suppression of proliferation of microbes like bacteria, fungi, and yeast. As an ideal condition required for such preservative composition, the composition should not have any toxicity and should exhibit the effect even with a trace amount.

When the composition of the present invention is used as a quasi-drug additive, the antimicrobial peptide may be directly added or used with other quasi-drug or quasi-drug components, and it can be suitably used according to a general method. Blending amount of the effective component can be suitably determined depending on the purpose of use.

The quasi-drug composition of the present invention is preferably a sterilizing cleanser, a shower foam, a mouth wash, a water tissue, a liquid soap, a hand wash, a humidifier filler, a mask, an ointment, a patch, or a filter filler, although it is not limited thereto.

The present invention further provides a method for antimicrobial treatment in a subject including administering a pharmaceutically effective amount of the aforementioned antimicrobial peptide to a subject. The subject may be a mammal excluding human, but it is not limited thereto.

Hereinbelow, the present invention is explained in greater detail in view of the Examples. However, it is evident that the following Examples are given only for exemplification of the present invention and by no means the present invention is limited to the following Examples.

EXAMPLES

Example 1. Synthesis, Isolation, and Purification of Peptide

According to the solution phase peptide synthesis by Merrifield (Merrifield, R B., J. Am. Chem. Soc., 85:2149-2154, 1963), the inventors of the present invention deleted the $1^{st}$ and $14^{th}$ amino acid residues in the amino acid sequence of Hp1404, which is a mother peptide described with the amino acid sequence of SEQ ID NO: 1. After that, the $4^{th}$ amino acid residue was substituted with lysine (K), the $7^{th}$ amino acid residue was substituted with leucine (L), and the $8^{th}$, $9^{th}$, and $12^{th}$ amino acid residues were sequentially substituted with lysine (K) for the synthesis (Table 1).

Specifically, as for the peptide in which the peptide designed in the present invention has a carboxy terminal in $NH_2$ form, a rink amide MBHA-resin was used as a starting material, and, as for the peptide having a carboxy terminal in OH form, a Fmoc (9-fluorenylmethoxycarbonyl)-amino acid-Wang resin was used as a starting material.

Peptide chain extension based on Fmoc-amino acid coupling was carried out by DCC (N-hydroxybenzotrizole (HOBt)-dicyclo-hexycarbodiimide) method. After coupling Fmoc-amino acid at the terminal amino acid of each peptide, the Fmoc group is removed by using NMP (20% piperidine/N-methyl pyrrolidone) solution. Then, after washing several times with NMP and DCM (dichloromethane), drying with nitrogen gas was carried out. Then, a solution in which TFA (trifluoroacetic acid), phenol, thioanisole, $H_2O$, and triisopropylsilane are mixed at ratio of 85:5:5:2.5:2.5 (v/v) was added thereto followed by reaction for 2 to 3 hours to remove the protective group and separate the peptide from resin. Then, the peptide was allowed to precipitate in diethyl ether. The crude peptide obtained by the above method was purified by using a purification type reverse phase (RP)-HPLC column (Delta Pak, $C_{18}$ 300 Å, 15, 19.0 mm×30 m, Waters, USA) based on acetonitrile gradient containing 0.05% TFA. The synthesized peptide was hydrolyzed with 6 N HCl at 110° C. Then, the resulting residues were concentrated under reduced pressure and dissolved in 0.02 N HCl. The amino acid composition was measured by using an amino acid analyzer (Hitachi 8500 A). To determine the purity and molecular weight of the peptide, MALDI mass analysis was carried out.

As a result, as shown in the following Table 1, the peptide represented by the amino acid described with SEQ ID NO: 1 to SEQ ID NO: 7 was synthesized with purity of 95% or higher, and the molecular weight was found to be the same as the expected molecular weight.

TABLE 1

Sequence, molecular weight, and retention time of peptides synthesized in the present invention

| Peptide name | Amino acid sequence | SEQ ID NO. | Retention time | Molecular weight |
| --- | --- | --- | --- | --- |
| Hp1404 | GILGKLWEGVKSIF-$NH_2$ | 1 | 36.251 | 1545.7 |
| Hp1404-T1 | ILGKLWEGVKSI-$NH_2$ | 2 | 23.176 | 1342.2 |
| Hp1404-T1a | ILKKLWEGVKSI-$NH_2$ | 3 | 20.756 | 1413.5 |
| Hp1404-T1b | ILKKLLEGVKSI-$NH_2$ | 4 | 20.875 | 1340.2 |

TABLE 1-continued

Sequence, molecular weight, and retention time of peptides synthesized in the present invention

| Hp1404-T1c | ILKKLLKGVKSI-NH₂ | 5 | 17.643 | 1338.0 |
| Hp1404-T1d | ILKKLLKKVKSI-NH₂ | 6 | 17.741 | 1409.8 |
| Hp1404-T1e | ILKKLLKKVKKI-NH₂ | 7 | 16.002 | 1451.0 |

| Amino Acid No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Hp1404 | G | I | L | G | K | L | W | E | G | V | K | S | I | F |
| Hp1404-T1 | — | — |   |   | — | — | — | — | — | — | — | — | — |   |
| Hp1404-T1a | — | — | K |   | — | — | — | — | — | — | — | — | — |   |
| Hp1404-T1b | — | — | K |   | — | — | L | — | — | — | — | — | — |   |
| Hp1404-T1c | — | — | K |   | — | — | L | K | — | — | — | — | — |   |
| Hp1404-T1d | — | — | K |   | — | — | L | K | K | — | — | — | — |   |
| Hp1404-T1e | — | — | K |   | — | — | L | K | K | — |   | K | — |   |

[Blank: deletion of amino acid, - : no substitution of amino acid]

Example 2. Measurement of Antimicrobial Activity

To compare the antimicrobial activity among the peptides produced by the method of Example 1, the inventors of the present invention measured the minimal growth inhibitory concentration (MIC), which is minimum concentration of the peptide showing no dissociation of bacterial cells.

Specifically, the bacterial strain described in the following Table 2 was purchased and cultured to a mid-log phase in each medium with a composition suitable for each strain. Then, after dilution to bacterial cell concentration of $2 \times 10^4$ cells/100 µl, the cells were inoculated to a microtiter plate (NUNC, USA). Thereafter, Hp1404-T1, Hp1404-T1a, Hp1404-T1b, Hp1404-T1c, Hp1404-T1d or Hp1404-T1e peptide which has been synthesized in Example 1 above was subjected to serial dilution, ½ times for each, with BSA (bovine serum albumin) solution in a 96-well plate. After adding the cells to a plate, the cells were cultured for 18 hours at 37° C. By using a microtiter plate reader (Merck Elisa reader, Germany), the absorbance was measured at a wavelength of 600 nm to determine the MIC value of each bacterial strain. As a control group, Hp1404 as a mother peptide was used.

TABLE 2

Bacterial strains used in the present invention and sources of the bacterial strains

| Category | Name of bacterial strain | Source | Accession number |
|---|---|---|---|
| Gram-negative bacteria | Escherichia coli | American Type Culture Collection | ATCC 25922 |
| Gram-positive bacteria | Pseudomonas aeruginosa | American Type Culture Collection | ATCC 27853 |
| | Staphylococcus aureus | American Type Culture Collection | ATCC 25923 |
| | Listeria monocytogenes | Korean Collection for Type Cultures | KCTC 3710 |
| Bacteria having tolerance to antibiotics | Pseudomonas aeruginosa | Isolated strain 138 | |
| | | Isolated strain 431 | |
| | | Isolated strain 434 | |
| | | Isolated strain 557 | |
| | | Isolated strain 559 | |
| | | Isolated strain778 | |
| | | Isolated strain 1034 | |
| | | Isolated strain 1162 | |
| | | Isolated strain 3290 | |
| | | Isolated strain 3399 | |
| | | Isolated strain 3592 | |
| | | Isolated strain 3904 | |
| | | Isolated strain 4007 | |
| | | Isolated strain 4319 | |
| | | Isolated strain 4891 | |
| | | Isolated strain 5018 | |
| | | Isolated strain 671973 | |

As a result, compared to the mother peptid control group Hp1404, HpH1404-T1c, Hp1404-T1d, and Hp1404-T1e peptides were found to exhibit a similar or better antimicrobial activity for *Staphylococcus aureus* and *Pseudomonas aeruginosa* as it is shown in the following Table 3.

TABLE 3

MIC of antimicrobial peptides for Gram-negative bacteria, Gram-positive bacteria, and bacteria having tolerance to antibiotics

| | | Minimal inhibitory concentration (µM) | | | | | | |
|---|---|---|---|---|---|---|---|---|
| Strain | Peptide | Hp1404 | Hp1404 -T1 | Hp1404 -T1a | Hp1404 -T1b | Hp1404 -T1c | Hp1404 -T1d | Hp1404 -T1e |
| Gram-negative bacteria | E. coli | 6.25 | >25 | >25 | >25 | >25 | >25 | >25 |
| | P. aeruginosa | 12.5 | >25 | >25 | >25 | 3.13 | 1.56 | 1.56 |
| Gram-positive bacteria | S. aureus | 3.13 | >25 | >25 | >25 | 12.5 | 6.25 | 3.13 |
| | L. monocytogenes | 3.13 | >25 | >25 | >25 | 25 | >25 | >25 |

TABLE 3-continued

MIC of antimicrobial peptides for Gram-negative bacteria, Gram-positive bacteria, and bacteria having tolerance to antibiotics

| | | Minimal inhibitory concentration (µM) | | | | | | |
|---|---|---|---|---|---|---|---|---|
| Strain | Peptide | Hp1404 | Hp1404-T1 | Hp1404-T1a | Hp1404-T1b | Hp1404-T1c | Hp1404-T1d | Hp1404-T1e |
| Bacteria having tolerance to antibiotics | P. aeruginosa 138 | 12.5 | >25 | >25 | >25 | 25 | 12.5 | 6.25 |
| | P. aeruginosa 431 | 12.5 | >25 | 25 | >25 | 12.5 | 3.13 | 3.13 |
| | P. aeruginosa 434 | 12.5 | >25 | 25 | 25 | 6.25 | 3.13 | 3.13 |
| | P. aeruginosa 557 | 6.25 | >25 | >25 | >25 | 25 | 3.13 | 3.13 |
| | P. aeruginosa 559 | 25 | >25 | >25 | >25 | 25 | 12.5 | 6.25 |
| | P. aeruginosa 778 | 12.5 | >25 | >25 | >25 | 6.25 | 3.13 | 1.56 |
| | P. aeruginosa 1034 | 6.25 | >25 | >25 | >25 | 6.25 | 3.13 | 1.56 |
| | P. aeruginosa 1162 | 12.5 | >25 | >25 | >25 | 3.13 | 1.56 | 1.56 |
| | P. aeruginosa 3290 | 12.5 | >25 | >25 | >25 | >25 | 6.25 | 6.25 |
| | P. aeruginosa 3399 | 6.25 | >25 | 25 | >25 | 3.13 | 1.56 | 0.78 |
| | P. aeruginosa 3543 | 6.25 | >25 | >25 | >25 | >25 | 25 | 12.5 |
| | P. aeruginosa 3592 | 6.25 | >25 | 12.5 | 25 | 6.25 | 3.13 | 1.56 |
| | P. aeruginosa 3904 | 6.25 | >25 | 25 | >25 | 6.25 | 6.25 | 3.13 |
| | P. aeruginosa 4007 | 25 | >25 | >25 | >25 | 12.5 | 6.25 | 3.13 |
| | P. aeruginosa 4319 | 12.5 | >25 | >25 | >25 | 6.25 | 3.13 | 3.13 |
| | P. aeruginosa 4891 | 6.25 | >25 | 25 | >25 | 6.25 | 3.13 | 1.56 |
| | P. aeruginosa 5018 | 12.5 | >25 | >25 | >25 | 3.13 | 1.56 | 1.56 |
| | P. aeruginosa 671973 | 3.13 | >25 | 25 | >25 | 6.25 | 1.56 | 1.56 |

Example 3: Measurement of Anti-Biofilm Activity

To compare the antimicrobial activity among the peptides produced by the method of Example 1, the inventors of the present invention measured the biofilm inhibitory concentration value of the peptide showing no dissociation of bacterial cells.

Specifically, among the bacterial strains described in the above Table 2, bacteria showing favorable biofilm forming were cultured to a mid-log phase in each medium. Then, after dilution to bacterial cell concentration of $5 \times 10^4$ cells/100 µl, the cells were inoculated to a microtiter plate (PSL). Thereafter, Hp1404, Hp1404-T1c, Hp1404-T1d or Hp1s404-T1e peptide which has been synthesized in Example 1 above was diluted, ¹⁄₁₀ times for each, with 10 mM sodium phosphate (pH 7.2) solution in a 96-well plate. After adding the cells (10 µl) to a plate, the cells were cultured for 24 hours at 37° C. After removing the supernatant completely, the cells were fixed with 100% methanol for 15 minutes and reacted for 1 hour with Crystal violet staining solution followed by rinsing for 3 times. Then, after dissolving in 95% ethanol, the absorbance was measured at a wavelength of 595 nm by using a microtiter plate reader to determine the biofilm minimal inhibitory concentration value of each bacterial strain.

As a result, as it is shown in the following Table 4, Hp1404-T1c, Hp1404-T1d and Hp1404-T1e peptides were found to exhibit a similar or stronger biofilm inhibitory activity in all bacterial strains compared to Hp1404 as a control group peptide.

TABLE 4

Anti-biofilm activity of antimicrobial peptides for Gram-negative bacteria, Gram-positive bacteria, and bacteria having tolerance to antibiotics

| | Biofilm minimal inhibitory concentration (µM) | | | |
|---|---|---|---|---|
| | Hp1404 | Hp1404-T1c | Hp1404-T1d | Hp1404-T1e |
| S. aureus (ATCC 25923) | 3.13 | 12.5 | 6.25 | 12.5 |
| P. aeruginosa (ATCC 27853) | 25 | 25 | 12.5 | 12.5 |
| P. aeruginosa 434 | 25 | 50 | 12.5 | 12.5 |
| P. aeruginosa 559 | 50 | 25 | 12.5 | 12.5 |
| P. aeruginosa 778 | 25 | 25 | 12.5 | 6.25 |
| P. aeruginosa 1034 | 25 | 25 | 12.5 | 6.25 |
| P. aeruginosa 1162 | 25 | 12.5 | 6.25 | 6.25 |
| P. aeruginosa 3543 | 6.25 | >50 | >50 | 50 |
| P. aeruginosa 3399 | 12.5 | 25 | 25 | 12.5 |
| P. aeruginosa 4007 | 25 | >50 | 50 | 12.5 |

Example 4. Measurement of Hemolytic Activity

To compare the cytotoxicity among the peptides that are produced by the method of Example 1, erythrocyte hemolytic activity of the synthesized peptide was measured.

Specifically, erythrocytes of a mouse (Balb/c, 6 week old, female) were diluted in physiological saline (PBS, pH 7.0) to have concentration of 8%, and then subjected to a treatment with Hp1404, Hp1404-T1, Hp1404-T1a, Hp1404-T1b, Hp1404-T1c, Hp1404-T1d or Hp1404-T1e, each at concentration of 6.25, 12.5, 25.0, 50.0, 100.0 and 200.0 µM/well, respectively, followed by a reaction for 1 hour at 37° C. After that, the amount of hemoglobin contained in a supernatant collected by centrifuge at 1,000×g was determined by measuring the absorbance at a wavelength of 414 nm. As a control group to be used as a reference for cell disruption level, the supernatant collected by a treatment with 1% Triton X-100 (Sigma, USA) and a reaction for 1 hour at 37° C. was used to measure the absorbance. By setting the resulting absorbance value at 100%, the hemolytic activity of each peptide was calculated using the following mathematical formula 1.

Erythrocyte disrupting ability (hemolysis) (%)=(Absorbance A−Absorbance B)/(Absorbance C−Absorbance B)×100    [Mathematical formula 1]

(in the above formula, Absorbance A indicates the absorbance of a reaction solution treated with each peptide, in which the absorbance is measured at a wavelength of 414 nm; Absorbance B indicates the absorbance of a reaction solution treated with PBS, in which the absorbance is measured at a wavelength of 414 nm; and Absorbance C indicates the absorbance of a reaction solution treated with 1% Triton X-100, in which the absorbance is measured at a wavelength of 414 nm).

As a result, it was found as shown in Table 5 that, when mouse erythrocytes are treated with 200 μM Hp1404 peptide as a mother peptide, 100% hemolysis of the mouse erythrocytes was yielded. On the other hand, Hp1404-T1, Hp1404-T1a, Hp1404-T1b, Hp1404-T1c, Hp1404-T1d and Hp1404-T1e did not exhibit any erythrocyte disrupting ability even at a concentration of 200 μM, and thus it was confirmed that the antimicrobial peptide of the present invention has less cytotoxicity than the mother peptide.

TABLE 5

Hemolytic activity of antimicrobial peptides

| | Erythrocyte disrupting ability % (peptide concentration, μM) | | | | | |
|---|---|---|---|---|---|---|
| | 200 | 100 | 50 | 25 | 12.5 | 6.25 |
| Hp1404 | 100 | 92.64 | 55.41 | 11.01 | 2.16 | 0.01 |
| Hp1404-T1 | 0.53 | 0 | 0 | 0 | 0 | 0 |
| Hp1404-T1a | 0.55 | 0 | 0 | 0 | 0 | 0 |
| Hp1404-T1b | 1.05 | 0 | 0 | 0 | 0.19 | 0.07 |
| Hp1404-T1c | 0.65 | 0 | 0 | 0 | 0 | 0 |
| Hp1404-T1d | 0.08 | 0 | 0 | 0 | 0 | 0 |
| Hp1404-T1e | 0.55 | 0.15 | 0 | 0.41 | 0.28 | 0.10 |

Example 5: Determination of Cytotoxicity in Normal Cell Line

To determine the cytotoxicity of the peptide produced by the method of Example 1 in normal cell line, toxicity was measured by using human keratinocytes (HaCaT cell line, Dr. N E. Fusenig, Heidelberg, Germany).

Specifically, HaCaT cells which have been cultured in DMEM medium containing 10% FBS (Fetal Bovine Serum) were aliquoted in a 96-well plate to have $2\times10^5$ cells per well. After culturing them for 24 hours, the cells were subjected to a treatment with Hp1404, Hp1404-T1, Hp1404-T1a, Hp1404-T1b, Hp1404-T1c, Hp1404-T1d, or Hp1404-T1e, each at concentration of 6.25, 12.5, 25.0, 50.0, 100.0 or 200.0 μM/well, followed by reaction for 24 hours in a 5% $CO_2$ incubator. After 24 hours, a reaction solution containing 0.5 mg/ml MTT (Thiazolyl Blue Tetrazolium Bromide) dissolved in physiological saline (PBS) was added in an amount of 100 μl to each well and the reaction was allowed to occur for 4 hours. After that, the supernatant was removed, and, by dissolving MTT crystals that are formed by adding 200 μl of DMSO (dimethyl sulfoxide), the absorbance at 560 nm was measured to determine the cell survival ability.

As a result, it was found as shown in the following Table 6 that, when the cells are treated with Hp1404 as a mother peptide (200 μM), 0% cell survival ability was shown, indicating that Hp1404 peptide exhibits very high cytotoxicity. On the other hand, Hp1404-T1a, Hp1404-T1b, Hp1404-T1c and Hp1404-T1d peptides exhibited the cell survival ability of 30.67%, 31.95%, 39.87% and 18.35%, respectively, at a concentration of 200 μM, indicating that they have very low cytotoxicity. In particular, Hp1404-T1c and Hp1404-T1d peptides were found to exhibit the cell survival ability of 100% at a concentration of 200 μM, indicating that they have almost no cytotoxicity compared to mother Hp1404 peptide.

TABLE 6

Analysis of cytotoxicity of antimicrobial peptides

| | Cell survival ability % (peptide concentration, μM) | | | | | |
|---|---|---|---|---|---|---|
| | 200 | 100 | 50 | 25 | 12.5 | 6.25 |
| Hp1404 | 0 | 0.11 | 30.48 | 100 | 100 | 100 |
| Hp1404-T1 | 100 | 100 | 100 | 100 | 100 | 100 |
| Hp1404-T1a | 30.67 | 100 | 100 | 100 | 100 | 100 |
| Hp1404-T1b | 31.95 | 80.86 | 100 | 100 | 100 | 100 |
| Hp1404-T1c | 39.87 | 48.56 | 51.28 | 100 | 100 | 100 |
| Hp1404-T1d | 18.35 | 34.56 | 33.09 | 38.90 | 53.93 | 100 |
| Hp1404-T1e | 100 | 100 | 100 | 100 | 100 | 100 |

Example 6. Measurement of Circular Dichroism Spectrum

To determine whether or not an α-helical structure as a secondary structure is induced by the peptides produced by the method of Example 1, measurement was carried out using circular dichroism.

Specifically, Hp1404, Hp1404-T, Hp1404-T1a, Hp1404-T1b, Hp1404-T1c, Hp1404-T1d or Hp1404-T1e peptide was added at a concentration of 40 μM to 10 mM sodium phosphate (pH 7.4), 50% 2,2,2-trifluoroethanol (TFE), or 30 mM sodium dodecyl sulfate (SDS) solution. After adding the mixture to a cell with 0.1 cm path length, the temperature was set at 25° C. and a circular dichroism spectrum was measured by using Jasco 810 spectrophotometer. As a formula to calculate an α-helical structure for the above circular dichroism spectrum, the following mathematical formula 2 was used.

$$[\theta] = \frac{\theta_{obs}}{10 \cdot l \cdot c}$$    [Mathematical formula 2]

(in the formula, $\theta_{obs}$ represents the milidegress of a signal; l represents the optical path-length of a cell (cm); and c represents the concentration of added peptide (mol/l)).

As a result, no structure forming was seen when the peptide is added to 10 mM sodium phosphate solution but an α-helical structure as a secondary structure was formed by adding the peptide to 50% TFE solution and 30 mM SDS solution, although there is a slight difference between them. Based on those results, it was found that, in SDS and TFE solution, the antimicrobial peptide of the present invention can form an α-helical structure similar to a membrane of bacteria as microbes (FIG. 1).

Example 7. Determination of Stability Against Trypsin Enzyme

To determine whether or not the peptides prepared by the method of Example 1 have stability against an enzyme, RP-HPLC (reverse-phase HPLC) was carried out. Specifically, 20 μg of the peptide was reacted with 100 μl of trypsin at concentration of 20 nM for 1 to 2 hours at 37° C. After the reaction, 20 µl of the reaction product was applied to RP-HPLC, and the amount of remaining peptide was examined.

Figure 2:
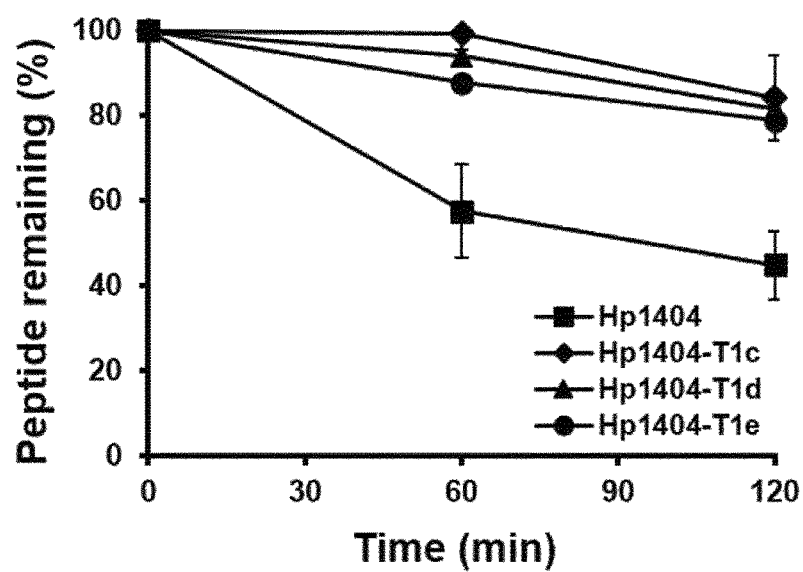
FIG. 2 shows the result of determining the stability of antimicrobial peptide against trypsin enzyme, in which the remaining amount of peptides after reaction for 2 hours was examined.

As a result, it was found that, after the reaction for 1 hour, 60% of Hp1404 as a mother peptide was maintained and at least 80% of Hp1404-T1c, Hp1404-T1d and Hp1404-T1e, which are a homologue peptide, were maintained. After the reaction for 2 hours, 80% of the homologue peptide was still maintained, but the mother peptide was reduced to 45%. Accordingly, it was acknowledged that the homologue peptides have better stability against trypsin enzyme than the mother peptide (FIG. 2).

Example 8. Determination of Anti-Biofilm by Vital Staining

By using the peptides prepared by the method of Example 1, the inhibition on biofilm forming was visually observed with a fluorescence microscope. As a type strain, *Staphylococcus aureus* and *Pseudomonas aeruginosa* were selected, and each peptide was treated at a concentration of 1× or 2×MBIC (Minimum Biofilm Inhibitory Concentration) with bacteria followed by culture for 24 hours. After that, staining with SYTO™ 9 staining reagent (green) was carried out for 30 minutes and degree of biofilm forming was observed under a microscope.

Figure 3:
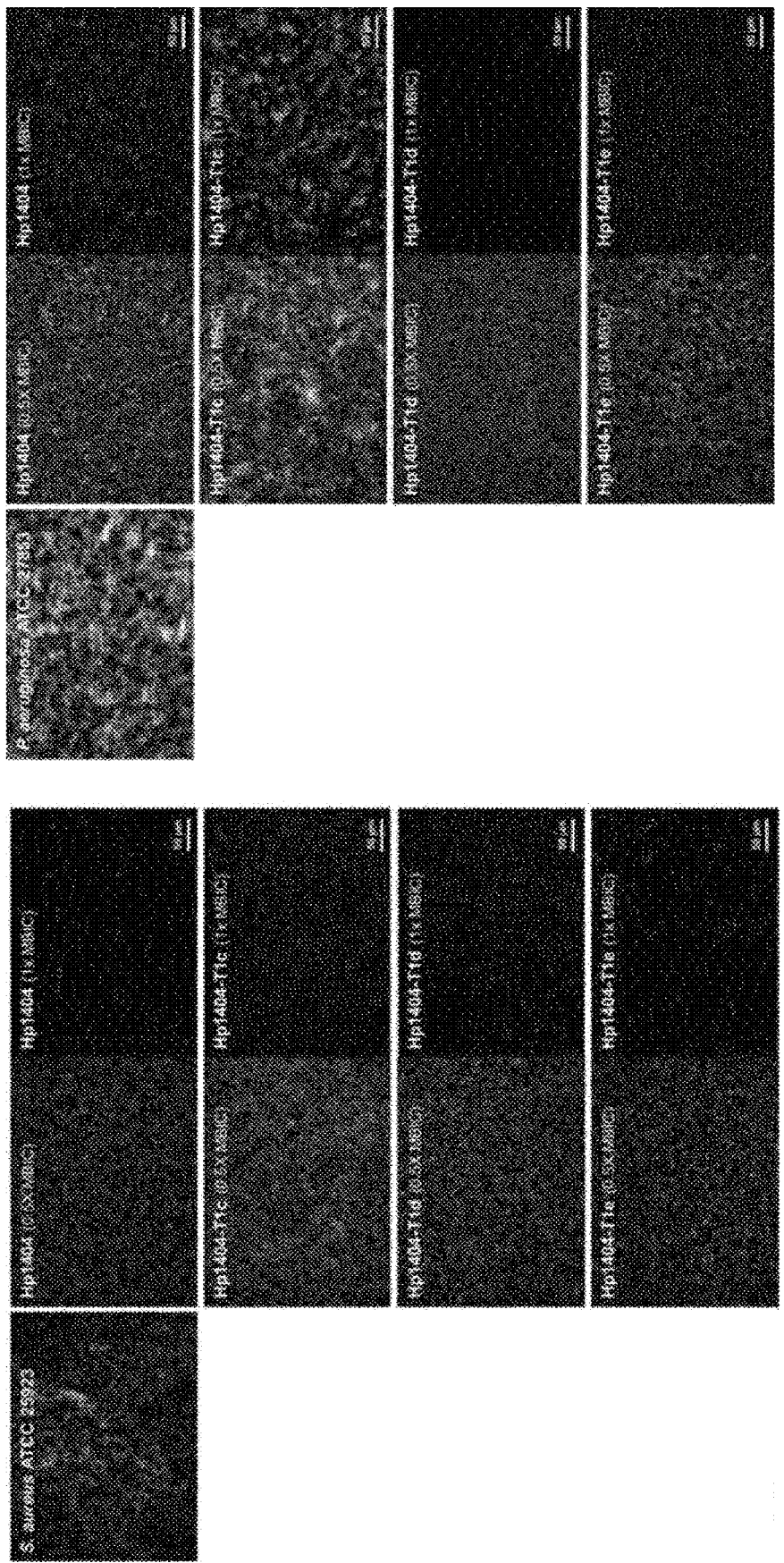
FIG. 3 shows the result of analyzing the effect of inhibiting biofilm forming by *Staphylococcus aureus* and *Pseudomonas aeruginosa* as a type strain, in which the effect was analyzed by using SYTO9 staining agent.

As a result, it was visually observed that the strain treated with the peptide at a concentration of 1×MBIC shows significantly inhibited biofilm forming compared to the strain treated with the peptide at a concentration of 0.5× MBIC. Based on this result, it was found that the antimicrobial peptide of the present invention exhibits a strong inhibitory effect on biofilm forming (FIG. 3).

Example 9. Measurement of Binding Ability Between Lipopolysaccharide (LPS) and Peptide By using the peptides prepared by the method of Example 1, binding to lipopolysaccharide (LPS), which is a constitutional component of a cell wall of Gram-negative bacteria, was examined. LPS used in the present invention was isolated from *P. aeruginosa*. Lipopolysaccharide (0 to 100 µg/ml) was diluted with 10 mM sodium phosphate buffer (pH 7.2), reacted with each peptide at a concentration of 1× or 2×MIC, and then cultured with the bacteria at 2×10$^5$ CFU/ml. By measuring the absorbance at 600 nm, the binding ability to the peptide was determined. Additionally, after reacting 0.1% polysaccharide with the peptide (40 µM) in an incubator, the secondary structure was examined by circular dichroism (CD) spectroscopy.

Figure 4:
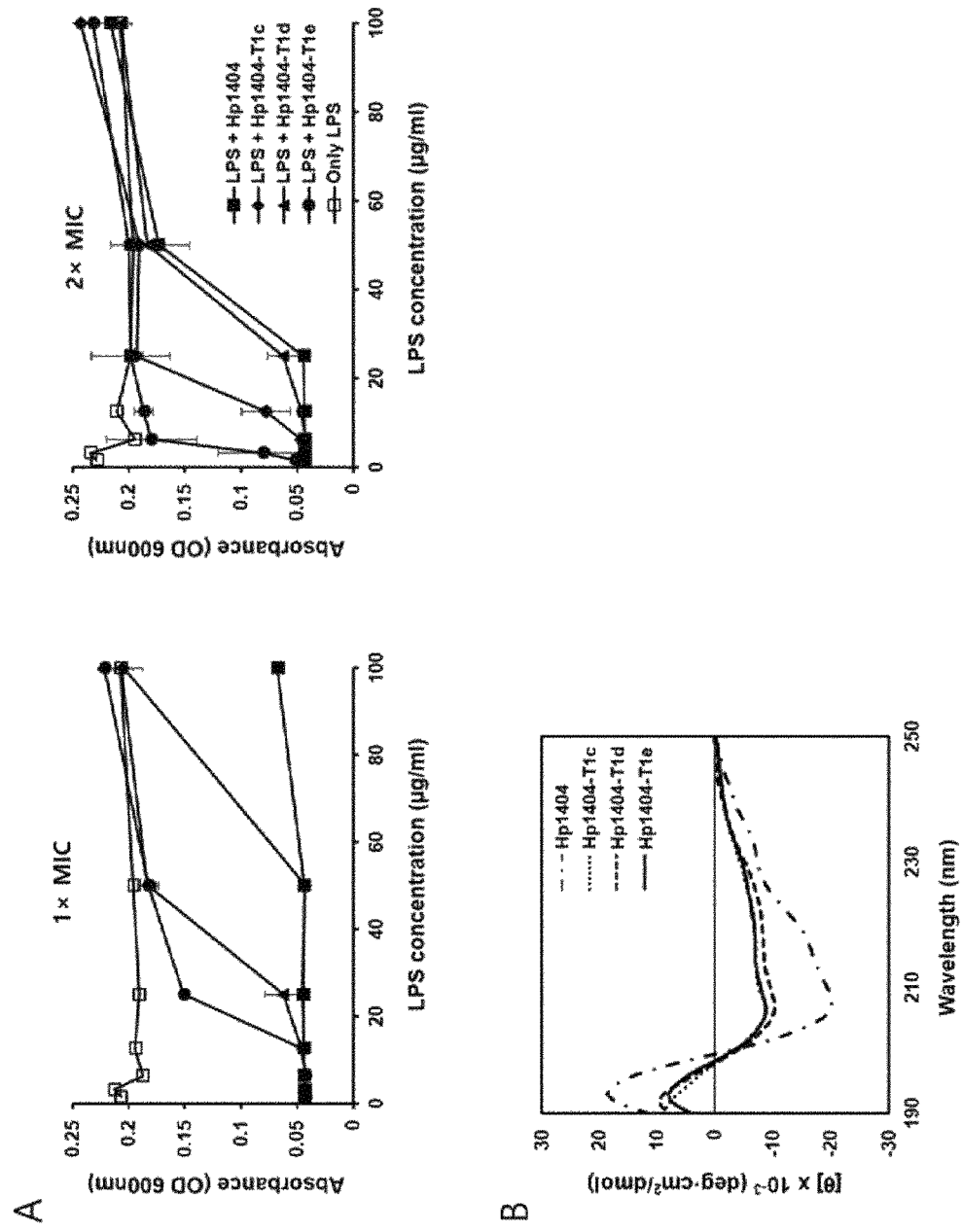
FIG. 4 shows the result of analyzing the binding ability between LPS (lipopolysaccharide), which is an endotoxin, and *Pseudomonas aeruginosa* (*P. aeruginosa*), and also the binding structure.

As a result, it was shown that, at the concentration of 2×MIC, each antimicrobial peptide binds to LPS at a concentration of 50 µg/ml, thus showing no peptide activity on the bacteria. Furthermore, at the concentration of 1×MIC, it was shown than binding to LPS increases in order of Hp1404-T1e, Hp1404-T1d, Hp1404-T1c, and Hp1404, thus also showing no peptide activity on the bacteria. Furthermore, the binding structure between LPS and the peptide was determined by CD spectroscopy, and, as a result, forming of an α-helical structure was confirmed (FIG. 4).

Example 10. Working Mechanism on Outer Membrane and Inner Membrane of Bacteria By using the peptides prepared by the method of Example 1, effect of the peptide on the outer membrane and inner membrane of bacteria was examined. Specifically, by using NPN (N-phenyl-1-naphthylamine) fluorescent dye, it was examined whether or not each antimicrobial peptide exhibits any effect on the outer membrane of *P. aeruginosa* as a type strain. According to the accumulation in bacterial membrane, NPN does not emit any fluorescence. However, once the hydrophobic part is exposed as a result of damage occurring in cell wall, NPN emits fluorescence. After culturing each strain in TSB and NB medium, the strain was adjusted such that it has OD$_{600}$ value of 0.2 in 5 mM HEPES buffer solution. After allowing the reaction to occur between 10 µM NPN dissolved in 95% ethanol and the bacteria by adding them in a 96-well black plate, the peptide at a concentration of 1×, 2× or 4×MIC and 0.1% Triton X-100 were further added, and then the fluorescence was measured.

Figure 5:
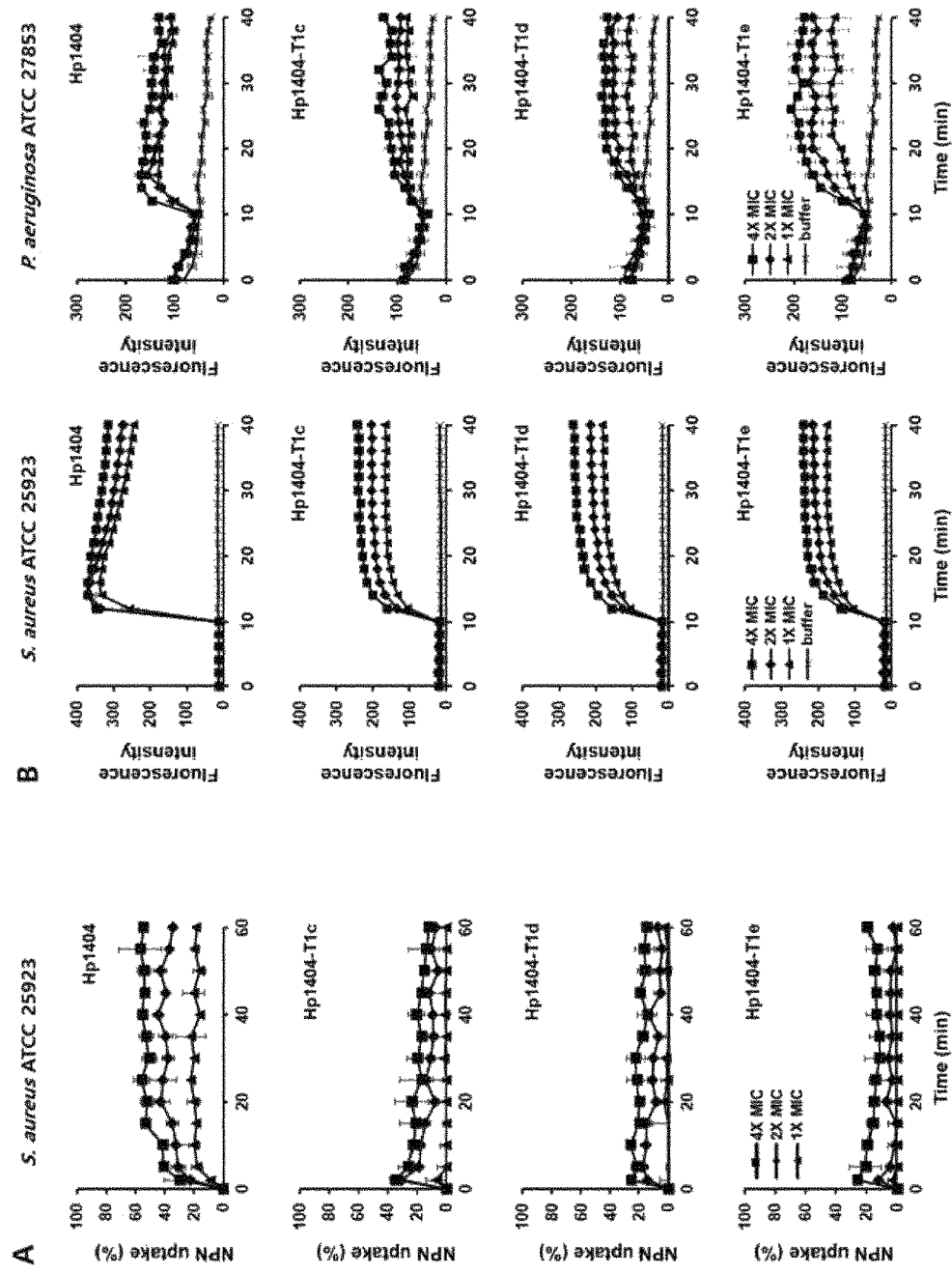
FIGS. 5 and 6 show the result of determining the working activity of the control group peptide Hp1404 and novel peptides Hp1404-T1c, Hp1404-T1d and Hp1404-T1e on membrane of *Staphylococcus aureus* (*S. aureus*) or *Pseudomonas aeruginosa* (*P. aeruginosa*).

As a result, it was found that Hp1404 showed the fluorescence value which increases in treatment concentration-dependent manner, while the homologue peptides exhibit less change in the fluorescence compared to Hp1404. Based on this result, it was found that the homolog peptides exhibit less effect on an outer membrane compared to the mother peptide (A of FIG. 5).

Furthermore, to determine any effect exhibited on an inner membrane of bacteria, the experiment was carried out by using DiSC$_3$-5 (3,3'-dipropylthiadicarbocyanine Iodide). DiSC$_3$-5 accumulates in a cell wall, and, once the cell wall is damaged, it is released to emit fluorescence. After culturing *S. aureus* and *P. aeruginosa* in an NB medium, they were washed with 5 mM HEPES buffer solution added with 20 mM glucose and then prepared in 5 mM HEPES buffer solution, which has been added with 20 mM glucose and 0.1 M potassium chloride, such that it has OD$_{600}$ value of 0.05. After the reaction with 1 µM DiSC$_3$-5 for 1 hour followed by stabilization, the peptide at a concentration of 1×, 2×, or 4×MIC was further added, and then the fluorescence was measured. As a result, it was found that the fluorescence of DiSC$_3$-5 increases in concentration-dependent manner. Based on this result, it was found that the peptides exhibit their effect on an inner membrane of bacteria (B of FIG. 5).

Example 11. Flow Cytometry Measurement

To determine whether or not the peptides prepared by the method of Example 1 have any effect on bacteria membrane, Hp1404-T1c, Hp1404-T1d and Hp1404-T1e, which have been found to exhibit the similar activity to the mother peptide and show no cytotoxicity even at high concentrations, were analyzed by flow cytometry.

Specifically, *S. aureus* or *P. aeruginosa* was treated for 1 hour at 37° C. with the mother peptide Hp1404, or Hp1404-T1c, Hp1404-T1d or Hp1404-T1e peptide (at concentration of 2×MIC). After that, the supernatant was removed by centrifuge (10,000 rpm) and stained with propidium iodide (PI, concentration of 10 µg/ml) for 30 minutes at 4° C. Thereafter, unbound propidium iodide was removed by centrifuge, and the problem of cell aggregation phenomenon was solved by adding physiological saline (PBS) in an amount of 1 ml. By using Bechman flow cytometry, the effect of the peptides exhibited on bacterial membrane was determined.

Figure 6:
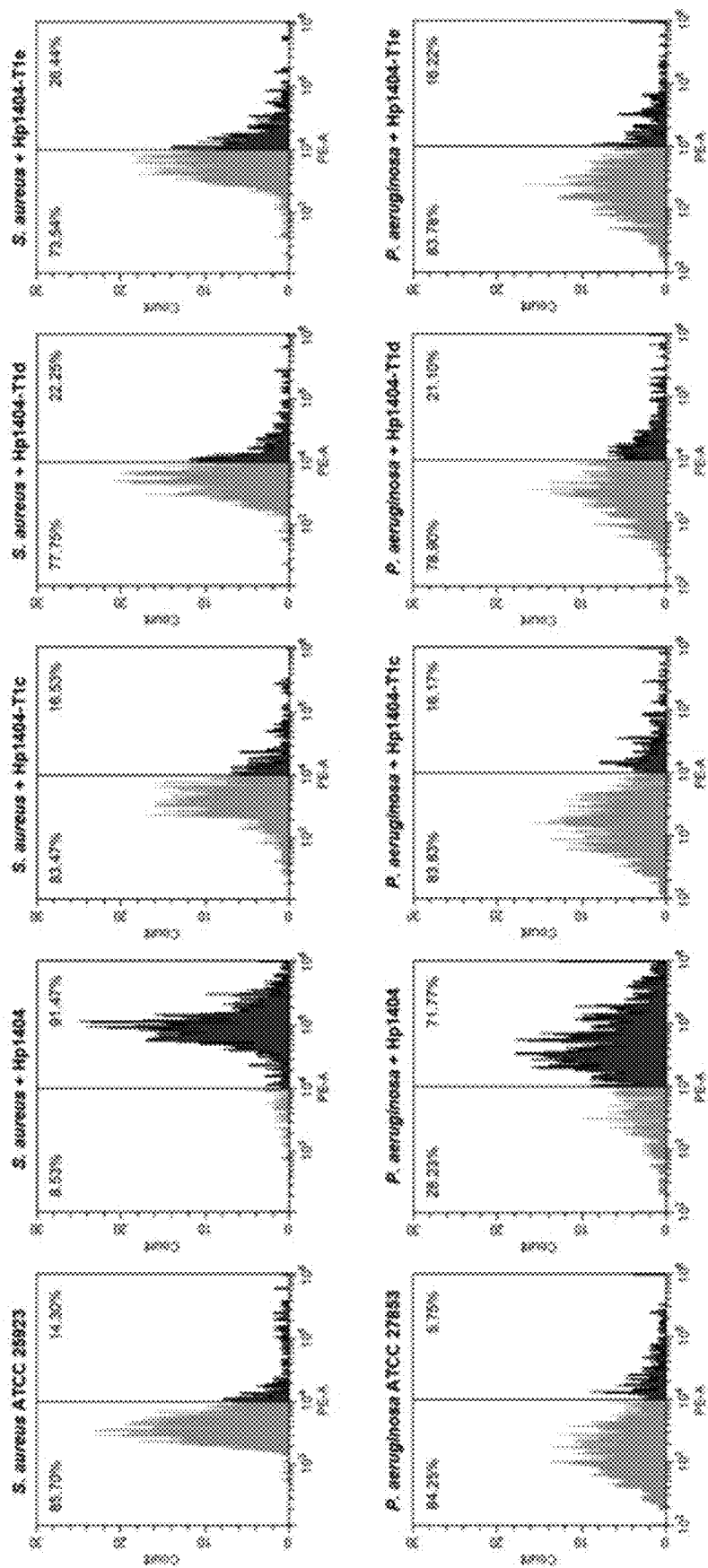

As a result, the bacteria membrane was damaged by HP1404 peptide, thus yielding the rightward shift of fluorescence signal while no such shift of fluorescence signal is caused by Hp1404-1c, Hp1404-T1d or Hp1404-T1e, indicating the absence of damage occurring in bacteria membrane (FIG. 6). Based on this result, it was speculated that the working mechanism of the novel peptides of the present invention on bacteria membrane is different from that of the mother peptide as a control group.

Example 12. Analysis of Binding Between Antimicrobial Peptide and DNA

To figure out the working mechanism of the synthetic peptides of the present invention for showing the antimicrobial activity, electrophoresis was carried out to examine the possible binding of synthetic peptides, i.e., Hp1404, Hp1404-1c, Hp1404-T1d and Hp1404-T1e, to DNA as an internal material of bacteria.

Specifically, after reacting the plasmid DNA (pRSETB, 260 ng) with the peptide at different ratio (i.e., peptide/DNA ratio is as follows for lane number 1 to lane number 8: DNA only, 0.25:1, 0.5:1, 1:1, 1.5:1, 2:1, 3:1, and 4:1. respectively) for 10 minutes at 37° C., they were subjected to electrophoresis using 1% agarose gel followed by ethidium bromide (EtBr) staining and UV visualization. As a positive control group, buforin 2, which is an antimicrobial peptide exhibiting an antimicrobial activity by binding to DNA, was used.

Figure 7:
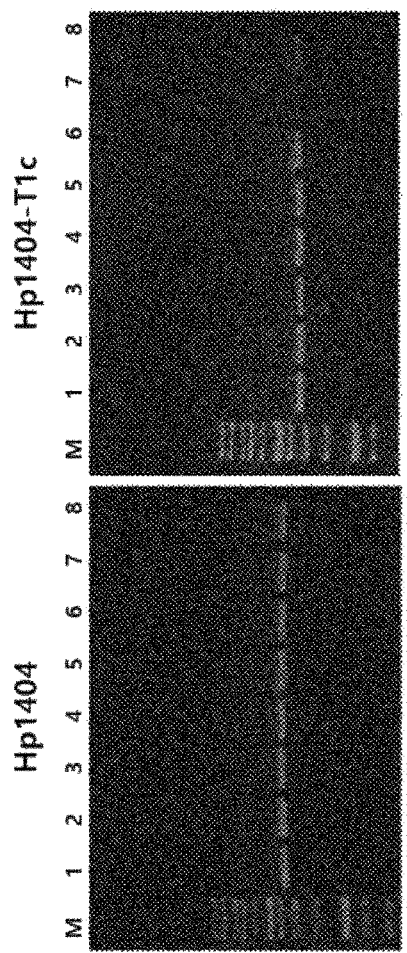
FIG. 7 shows the result of determining the binding ability of the control group peptide Hp1404 and novel peptides Hp1404-T1c, Hp1404-T1d and Hp1404-T1e for DNA as an internal material of bacteria, in which the peptide/DNA ratio in lane number 1 to lane number 8 is DNA only, 0.25:1, 0.5:1, 1:1, 1.5:1, 2:1, 3:1, and 4:1, respectively. In the figure, buforin 2 indicates an antimicrobial peptide which binds to DNA to exhibit the antimicrobial activity.
Figure 7:
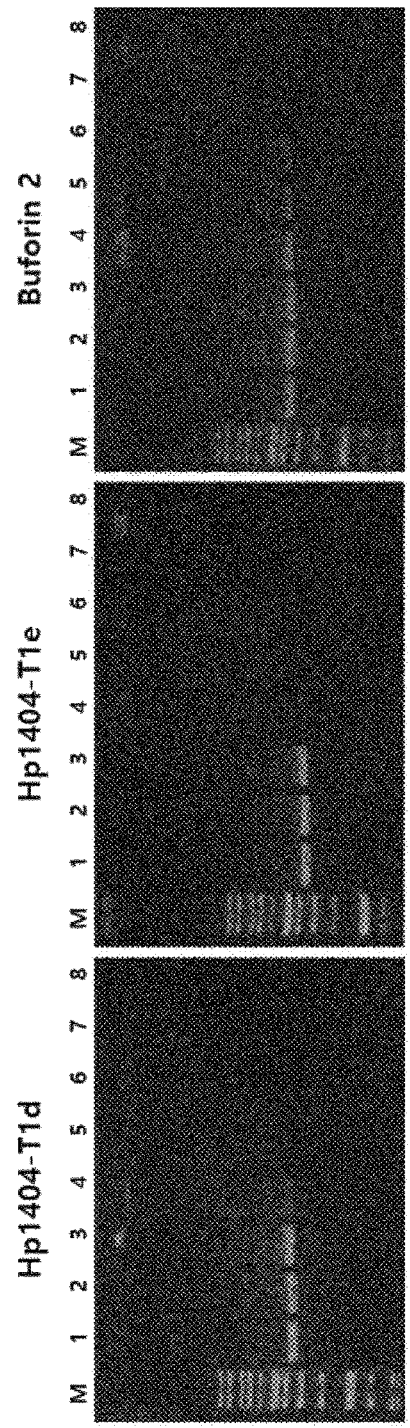

As a result, it was shown as illustrated in FIG. 7 that Hp1404 and Hp1404-T1c peptides did not bind to any DNA while Hp1404-T1d and Hp1404-T1e bind to DNA (FIG. 7). From this result, it was recognized that, unlike Hp1404 as a mother peptide which shows the antimicrobial activity by acting on bacteria membrane, Hp1404-T1d and Hp1404-Tie bind to DNA as an internal material of bacteria to exhibit the antimicrobial activity as caused by the substitution or deletion of some amino acid residues.

Example 13. Measurement of In Vivo Activity of Antimicrobial Peptide

By using Hp1404-T1e found to have the most excellent antimicrobial activity among the peptides that are prepared by the method of Example 1, in vivo antimicrobial activity was measured. Specifically, among the *Pseudomonas aeruginosa* strains, strain 1034 was selected and tested. The strain was prepared by washing 3 times with PBS buffer. Ciprofloxacin antibiotic was used as a control group. A BALB/c mouse (6 week old) was shaved clean and a wound with pre-determined size was created thereon. Then, the wound site was injected intracutaneously with *Pseudomonas aeruginosa* strain 1034 (20 ml, $2 \times 10^5$ CFU/ml). After the bacterial infection, the peptide and antibiotic, each prepared at a concentration of 0.1 mg/ml and 0.2 mg/ml, respectively, were intracutaneously injected, and the observation was made everyday. On each day, the skin tissues were sampled and smeared on an NB solid medium. The smeared medium was incubated in an incubator for 18 hours, and the number of grown colonies was counted and expressed in %.

Figure 8:
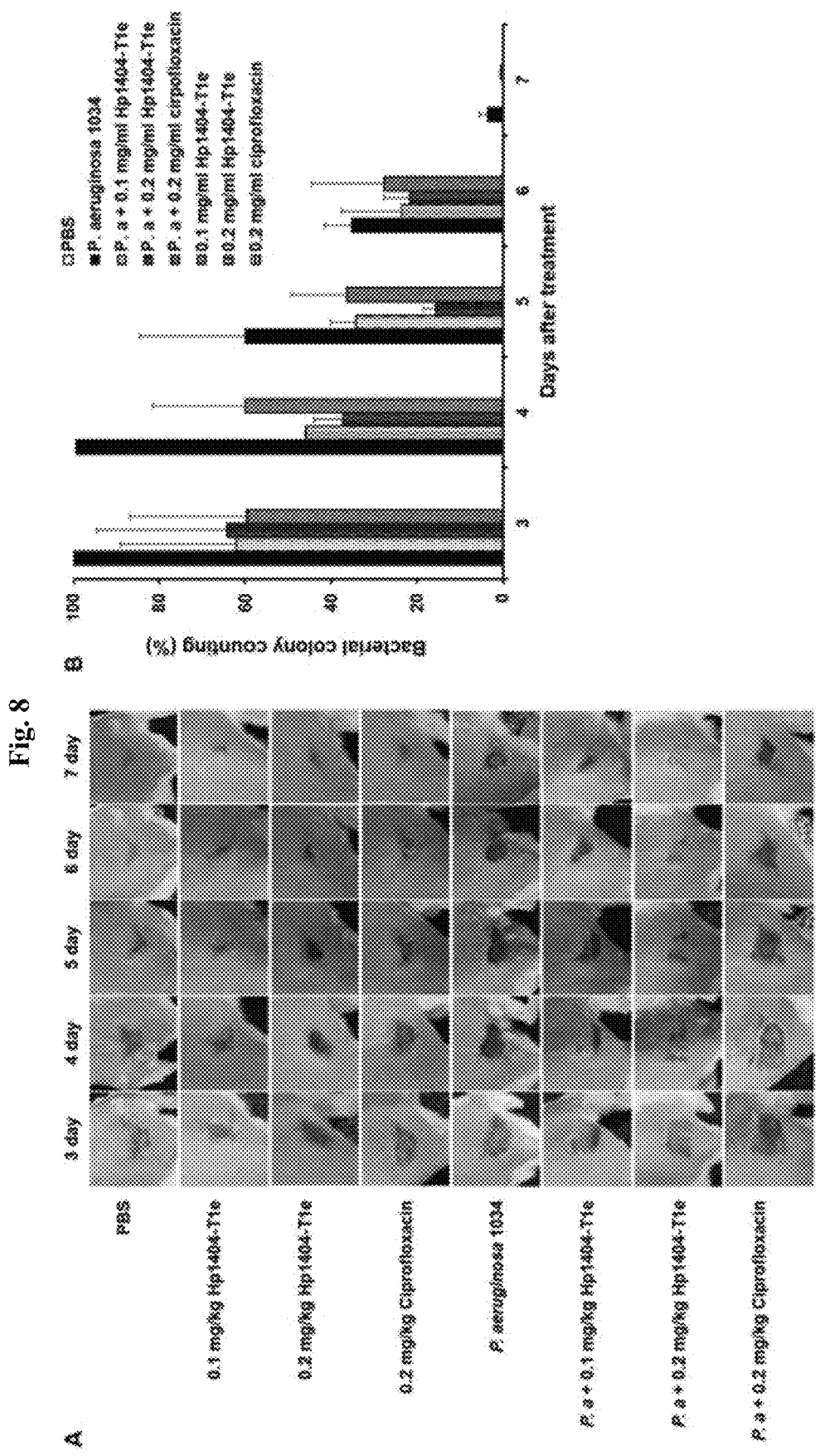
FIG. 8 shows the result of comparing the control group peptide Hp1404 and Hp1404-T1e, which has exhibited the most excellent effect in an in vivo activity test of an antimicrobial peptide, in which the comparison in made in terms of the antimicrobial activity exhibited on skin of a mouse infected by *P. aeruginosa*. In the figure, ciprofloxacin indicates an antibiotic used for a treatment of *Pseudomonas aeruginosa*.

As a result, the mouse injected only with the bacteria had a wound site which did not heal until Day 7 and remained in almost the same state, and the number of colonies was as high as 60% in the tissues sampled on Day 5. On the other hand, the mouse treated with Hp1404-T1e after previous infection with the bacteria showed the wound healing effect in peptide concentration-dependent manner, and the number of colonies determined from the tissues sample on Day 5 was found to be 40% (0.1 mg/ml treatment condition) or 20% (0.2 mg/ml treatment condition), indicating a significant reduction compared to the mouse infected with the bacteria only. In addition, the mouse which has been treated with ciprofloxacin after the bacterial infection showed no wound healing at all, and the number of colonies was also higher than that obtained from the peptide treatment condition (FIG. 8). Based on these results, it was recognized that Hp1404-T1e exhibits more excellent antimicrobial effect than antibiotics even in the body of a living organism.

Hereinbelow, Production examples for producing the composition of the present invention are exemplified.

<Production Example 1> Production of Pharmaceutical Preparation

<1-1> Production of Powder Preparation

| Peptide of the present invention | 20 mg |
| Lactose | 20 mg |

After mixing the above components, a powder preparation was produced by filling them in a sealed pack.

<1-2> Production of Tablet

| Peptide of the present invention | 10 mg |
| Corn starch | 100 mg |
| Lactose | 100 mg |
| Magnesium stearate | 2 mg |

After mixing the above components, a tablet was produced according to tabletting by a common method for producing a tablet.

<1-3> Production of Capsule Preparation

| Peptide of the present invention | 10 mg |
| Crystalline cellulose | 3 mg |
| Lactose | 14.8 mg |
| Magnesium stearate | 0.2 mg |

After mixing the above components, a capsule preparation was produced according to filling them in a gelatin capsule by a common method for producing a capsule preparation.

<1-4> Production of Liquid Preparation

| Peptide of the present invention | 20 mg |
| High fructose corn syrup | 10 g |
| Mannitol | 5 g |
| Purified water | suitable amount |

According to a common method for producing a liquid preparation, each component was added to purified water for dissolution. After adding a suitable amount of lemon flavor, the above components were admixed with one another followed by addition of purified water to adjust the entire volume to 100 ml. The mixture was then filled in a brown bottle followed by sterilization to produce a liquid preparation.

<1-5> Production of Injection Solution

| Peptide of the present invention | 10 μg/ml |
| Dil. hydrochloric acid BP | till to have pH 7.6 |
| Sodium chloride BP for injection | 1 ml at maximum |

In sodium chloride BP for injection with suitable volume, the peptide of the present invention was dissolved. pH of the resulting solution was adjusted to pH 7.6 by using dil. hydrochloric acid BP, and the volume was adjusted by using sodium chloride BP for injection followed by thorough mixing. The resulting solution was filled in a 5 ml Type I ampoule made of transparent glass. By melting the glass, the ampoule was sealed while having air in the top. Then, according to autoclave for 15 minutes or longer at 120° C., sterilization was carried out to produce an injection solution.

<Production Example 2> Production of Cosmetics

<2-1> Softening Cosmetic Water (Skin Lotion)

To produce a softening cosmetic water containing the peptide of the present invention, blending can be carried out as described in the following Table 7 and production can be made according to a common production method in the cosmetic field.

TABLE 7

Softening cosmetic water composition

| Component | Content (% by weight) |
| --- | --- |
| Peptide of the present invention | 0.1 to 30 |
| 1,3-Butylene glycol | 3.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | trace amount |
| Fragrance | trace amount |
| Purified water | To 100 |

<2-2> Nutritive Cosmetic Water (Lotion)

To produce an antimicrobial nutritive cosmetic water containing the peptide of the present invention, blending can be carried out as described in the following Table 8 and production can be made according to a common production method in the cosmetic field.

TABLE 8

Nutritive cosmetic water composition

| Component | Content (% by weight) |
| --- | --- |
| Peptide of the present invention | 0.1 to 30 |
| Squalane | 10.0 |
| Monooleic acid polyoxyethylene sorbitan | 2.0 |
| Lignum vitae oil | 0.1 to 30 |
| 1,3-Butylene glycol | 8.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | trace amount |
| Fragrance | trace amount |
| Purified water | To 100 |

<2-3> Essence

To produce an antimicrobial essence containing the peptide of the present invention, blending can be carried out as described in the following Table 9 and production can be made according to a common production method in the cosmetic field.

TABLE 9

Essence composition

| Component | Content (% by weight) |
| --- | --- |
| Peptide of the present invention | 0.1 to 30 |
| Sitosterol | 1.7 |
| Polyglyceryl 2-oleate | 1.5 |
| Ceramide | 0.7 |
| Ceteareth-4 | 1.2 |
| Cholesterol | 1.5 |
| Dicetyl phosphate | 0.4 |
| Conc. glycerin | 5.0 |
| Carboxyvinyl polymer | 0.2 |
| Xanthan gum | 0.2 |
| Preservative | trace amount |
| Fragrance | trace amount |
| Purified water | To 100 |

<2-4> Facial Cleanser (Cleansing Foam)

To produce an antimicrobial facial cleanser (cleansing foam) containing the peptide of the present invention, blending can be carried out as described in the following Table 10 and production can be made according to a common production method in the cosmetic field.

TABLE 10

Facial cleanser composition

| Component | Content (% by weight) |
| --- | --- |
| Peptide of the present invention | 0.1 to 30 |
| Sodium N-acylglutamate | 20.0 |
| Glycerin | 10.0 |
| PEG-400 | 15.0 |
| Propylene glycol | 10.0 |
| POE (15) oleyl alcohol ether | 3.0 |
| Laurin derivatives | 2.0 |
| Methyl paraben | 0.2 |
| EDTA—4Na | 0.03 |
| Fragrance | 0.2 |
| Purified water | To 100 |

<2-5> Nutritive Cream

To produce an antimicrobial nutritive cream containing the peptide of the present invention, as described in the following Table 11, production can be made according to a common production method in the cosmetic field.

TABLE 11

Nutritive cream composition

| Component | Content (% by weight) |
| --- | --- |
| Peptide of the present invention | 0.1 to 30 |
| Vaseline | 7.0 |
| Fluid paraffin | 10.0 |
| Bees wax | 2.0 |
| Polysorbate 60 | 2.5 |
| Sorbitan sesquioleate | 1.5 |
| Squalane | 3.0 |
| Propylene glycol | 6.0 |
| Glycerin | 4.0 |
| Triethanolamine | 0.5 |
| Xanthan gum | 0.5 |
| Tocopheryl acetate | 0.1 |
| Fragrance, preservative | trace amount |
| Purified water | To 100 |

<2-6> Massage Cream

To produce an antimicrobial massage cream containing the peptide of the present invention, as described in the following Table 12, production can be made according to a common production method in the cosmetic field.

TABLE 12

| Massage cream composition | |
|---|---|
| Component | Content (% by weight) |
| Peptide of the present invention | 0.1 to 30 |
| Propylene glycol | 6.0 |
| Glycerin | 4.0 |
| Triethanolamine | 0.5 |
| Bees wax | 2.0 |
| Tocopheryl acetate | 0.1 |
| Polysorbate 60 | 3.0 |
| Sorbitan sesquioleate | 2.5 |
| Cetaryl alcohol | 2.0 |
| Fluid paraffin | 30.0 |
| Xanthan gum | 0.5 |
| Fragrance, preservative | trace amount |
| Purified water | To 100 |

<2-7> Pack

To produce an antimicrobial pack containing the peptide of the present invention, as described in the following Table 13, production can be made according to a common production method in the cosmetic field.

TABLE 13

| Pack composition | |
|---|---|
| Component | Content (% by weight) |
| Peptide of the present invention | 0.1 to 30 |
| Propylene glycol | 2.0 |
| Glycerin | 4.0 |
| Polyvinyl alcohol | 10.0 |
| Ethanol | 7.0 |
| PEG-40 (Hydrogenated castor oil) | 0.8 |
| Triethanolamine | 0.3 |
| Fragrance, preservative | trace amount |
| Purified water | To 100 |

The present invention is not limited to Examples and Production examples that are described above and various modifications and changes can be made by a person skilled in the art. Also, an application can be made to cosmetics of various usages including color cosmetics. Furthermore, depending on the effect, use can be made for a pharmaceutical preparation which can be applied to human body by thin coating, i.e., ointment, and it is included in the spirit and scope of the present invention that is defined by the attached claims.

A sequence listing electronically submitted with the present application on Mar. 17, 2020 as an ASCII text file named 20200317_Q27620GR03_TU_SEQ, created on Mar. 16, 2020 and having a size of 2000 bytes, is incorporated herein by reference in its entirety.

The invention claimed is:

1. An antimicrobial peptide having the amino acid sequence of SEQ ID NO: 1, with the proviso that:
   (i) the 1st and the 14th amino acids are deleted;
   (ii) the 4th and the 8th amino acids are substituted with lysine (K);
   (iii) the 7th amino acid is substituted with leucine (L);
   (iv) the 9th amino acid is optionally substituted with lysine (K); and
   (v) the 12th amino acid is optionally substituted with lysine (K).

2. The antimicrobial peptide of claim 1, wherein the antimicrobial peptide is any one selected from the group consisting of the amino acid sequences of SEQ ID NO: 5 to SEQ ID NO: 7.

3. The antimicrobial peptide of claim 1, wherein the antimicrobial peptide has an antimicrobial activity against Gram-negative bacteria, Gram-positive bacteria, or bacteria having tolerance to antibiotics.

4. The antimicrobial peptide of claim 3, wherein the Gram-negative bacteria are *Pseudomonas aeruginosa*.

5. The antimicrobial peptide of claim 3, wherein the Gram-positive bacteria are *Staphylococcus aureus*.

6. The antimicrobial peptide of claim 3, wherein the bacteria having tolerance to antibiotics are *Pseudomonas aeruginosa* having tolerance to antibiotics.

7. The antimicrobial peptide of claim 1, wherein the antimicrobial peptide has low cytotoxicity for cells derived from human.

8. Antibiotics comprising the antimicrobial peptide of claim 1 as an effective component and at least one selected from the group consisting of aminoglycoside-based antibiotics, penicillin-based antibiotics, sulfonamide-based antibiotics, beat-lactam based antibiotics, chloramphenicol-based antibiotics, erythromycin-based antibiotics, florfenicol-based antibiotics, fosfmycin-based antibiotics, kanamycin-based antibiotics, lincomycin-based antibiotics, meticillin-based antibiotics, quinolone-based antibiotics, streptomycin-based antibiotics, tetracycline-based antibiotics, trimethoprim-based antibiotics, and vancomycin-based antibiotics.

9. An antibiotic cosmetic composition comprising the antimicrobial peptide of claim 1 as an effective component and a cosmetic component comprising at least one selected from the group consisting of an anti-oxidant, a stabilizing agent, a solubilizing agent, a vitamin, a pigment, a fragrance, and a carrier.

10. A food comprising the antimicrobial peptide of claim 1 as an effective component and a food additive component.

11. An antibiotic animal feed comprising the antimicrobial peptide of claim 1 as an effective component and an animal feed component.

12. Antibiotic biopesticides comprising the antimicrobial peptide of claim 1 as an effective component and a biopesticide component.

13. An antibiotic quasi-drug composition comprising the antimicrobial peptide of claim 1 as an effective component and a quasi-drug component comprising at least one selected from the group consisting of a sterilizing cleanser, a shower foam, a mouth wash, a water tissue, a liquid soap, a hand wash, a humidifier filler, a mask, an ointment, a patch, and a filter filler.

14. A method for treating an infection or an inflammation caused by a bacteria, the method comprising administering or applying to a subject in need thereof a composition comprising an antimicrobial peptide having the amino acid sequence of SEQ ID NO: 1, with the proviso that:
  (i) the $1^{st}$ and the $14^{th}$ amino acids are deleted;
  (ii) the $4^{th}$ and the $8^{th}$ amino acids are substituted with lysine (K);
  (iii) the $7^{th}$ amino acid is substituted with leucine (L);
  (iv) the $9^{th}$ amino acid is optionally substituted with lysine (K); and
  (v) the $12^{th}$ amino acid is optionally substituted with lysine (K).

15. The method of claim 14, wherein the antimicrobial peptide is any one selected from the group consisting of the amino acid sequences of SEQ ID NO: 5 to SEQ ID NO: 7.

16. The method of claim 14, wherein the bacteria is Gram-negative bacteria, Gram-positive bacteria, or antibiotics-resistant bacteria.

17. The method of claim 16, wherein the Gram-negative bacteria are *Pseudomonas aeruginosa*.

18. The method of claim 16, wherein the Gram-positive bacteria are *Staphylococcus aureus*.

19. The method of claim 16, wherein the antibiotics-resistant bacteria are *Pseudomonas aeruginosa* having tolerance to antibiotics.

20. The method of claim 14, wherein the composition further comprises a component from the group consisting of antibiotics, an antibiotic cosmetic, an antibiotic food additive, an antibiotic animal feed additive, an antibiotic biopesticide, and an antibiotic quasi-drug.

* * * * *

SEQUENCE LISTING

```
<160> NUMBER OF SEQ ID NOS: 7

<210> SEQ ID NO 1
<211> LENGTH: 14
<212> TYPE: PRT
<213> ORGANISM: scorpion Heterometrus petersii

<400> SEQUENCE: 1

Gly Ile Leu Gly Lys Leu Trp Glu Gly Val Lys Ser Ile Phe
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Hp1404-T1

<400> SEQUENCE: 2

Ile Leu Gly Lys Leu Trp Glu Gly Val Lys Ser Ile
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Hp1404-T1a

<400> SEQUENCE: 3

Ile Leu Lys Lys Leu Trp Glu Gly Val Lys Ser Ile
1               5                   10

<210> SEQ ID NO 4
<211> LENGTH: 12
<212> TYPE: PRT
```

```
<213> ORGANISM: Artificial Sequence
<220> FEATURE:
<223> OTHER INFORMATION: Hp1404-T1b

<400> SEQUENCE: 4

Ile Leu Lys Lys Leu Leu Glu Gly Val Lys Ser Ile
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Hp1404-T1c

<400> SEQUENCE: 5

Ile Leu Lys Lys Leu Leu Lys Gly Val Lys Ser Ile
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Hp1404-T1d

<400> SEQUENCE: 6

Ile Leu Lys Lys Leu Leu Lys Lys Val Lys Ser Ile
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Hp1404-T1e

<400> SEQUENCE: 7

Ile Leu Lys Lys Leu Leu Lys Lys Val Lys Lys Ile
1               5                   10
```